United States Patent
Barrett et al.

(10) Patent No.: US 7,832,864 B2
(45) Date of Patent: Nov. 16, 2010

(54) INVERSE OPTICAL DESIGN

(75) Inventors: Harrison H. Barrett, Tucson, AZ (US); Julia A. Sakamoto, Tucson, AZ (US); Alexander V. Goncharov, Galway (IE)

(73) Assignees: The Arizona Board of Regents on Behalf of the University of Arizona, Tucson, AZ (US); National University of Ireland, Galway, Galway (IE)

(*) Notice: Subject to any disclaimer, the term of this patent is extended or adjusted under 35 U.S.C. 154(b) by 0 days.

(21) Appl. No.: 12/139,602

(22) Filed: Jun. 16, 2008

(65) Prior Publication Data

US 2009/0009717 A1 Jan. 8, 2009

Related U.S. Application Data

(60) Provisional application No. 60/934,786, filed on Jun. 15, 2007.

(51) Int. Cl.
*A61B 3/10* (2006.01)

(52) U.S. Cl. .................... 351/205; 351/210; 351/221; 351/246

(58) Field of Classification Search ................ 351/205, 351/206, 210, 211, 212, 221, 246
See application file for complete search history.

(56) References Cited

U.S. PATENT DOCUMENTS

| | | | |
|---|---|---|---|
| 5,384,455 A | 1/1995 | Paxman | |
| 6,234,978 B1 * | 5/2001 | Mihashi et al. | ............ 600/558 |
| 6,273,566 B1 | 8/2001 | Kobayashi et al. | |
| 6,525,883 B2 | 2/2003 | Hirohara et al. | |
| 6,634,750 B2 | 10/2003 | Neal et al. | |
| 6,802,609 B2 | 10/2004 | Mihashi et al. | |
| 7,034,949 B2 | 4/2006 | Horwitz | |
| 7,113,268 B2 | 9/2006 | Gerwe et al. | |
| 7,270,413 B2 | 9/2007 | Hirohara et al. | |
| 7,311,402 B2 | 12/2007 | Mihashi et al. | |
| 2002/0041359 A1 | 4/2002 | Mihashi et al. | |
| 2004/0257530 A1 | 12/2004 | Chernyak et al. | |
| 2004/0263779 A1 | 12/2004 | Schroder | |
| 2005/0203422 A1 | 9/2005 | Wei | |
| 2007/0216866 A1 | 9/2007 | Kobayashi et al. | |
| 2007/0222948 A1 | 9/2007 | Dai | |

OTHER PUBLICATIONS

Artal et al. (Nov. 1, 1998) "Contributions of the Cornea and the Lens to the Aberrations of the Human Eye," *Opt. Lett.* 23(21):1713-1715.

(Continued)

*Primary Examiner*—Huy K Mai
(74) *Attorney, Agent, or Firm*—Greenlee Sullivan P.C.

(57) ABSTRACT

An imaging apparatus for simultaneously determining optical parameters of the eye comprising: a light source for illuminating at least a portion of the eye pupil; an illumination optical system for directing light rays emitted from the light source into the eye; a light receiving optical system for guiding the light rays reflected from the eye to a detector unit, wherein the detector unit detects an image intensity distribution from the light rays reflected from the eye; and an arithmetic unit for determining optical characteristics of the eye by parameter estimation is provided.

28 Claims, 7 Drawing Sheets

OTHER PUBLICATIONS

Atchison et al. (Jan. 2005) "Chromatic Dispersions of the Ocular Media of Human Eyes," *J. Opt. Soc. Am. A* 22(1):29-37.

Bará et al. (Jan. 2003) "Wide-Field Compensation of Monochromatic Eye Aberrations: Expected Performance and Design Trade-Offs," *J. Opt. Soc. Am. A* 20(1):1-10.

Barrett et al. (Feb. 2007) "Maximum-Likelihood Methods in Wavefront Sensing: Stochastic Models and Likelihood Functions," *J. Opt. Soc. Am. A* 24:391-414.

Barrett and K. J. Myers (2004) "Normal Random Vectors and Processes," In; *Foundations of Image Science*, Wiley, New Jersey, pp. 402-408, 894-903.

Brady et al. (2005) "Phase Retrieval as an Optical Metrology Tool," In; *Optifab: Technical digest*, SPIE Technical Digest TD03, pp. 139-141.

Chen (Jan. 2005) "Task-Based Lens Design with Application to Digital Mammography," *J. Opt. Soc. Am. A* 22(1):148-167.

Corana et al. (1987) "Minimizing Multimodal Functions of Continuous Variable with the 'Simulated Annealing' Algorithm," *ACM Transactions on Mathematical Software* 13(3):262-280.

Dubbelman et al. (2002) "Radius and Asphericity of the Posterior Corneal Surface Determined by Corrected Scheimpflug Photography," *Acta. Ophthalmol. Scand.* 80:379-383.

Dubbelman et al. (2001) "The Shape of the Aging Human Lens: Curvature, Equivalent Refractive Index and the Lens Paradox," *Vision Res.* 41:1867-1877.

Dubinin et al. (2008) "Human Retina Imaging: Widening of High Resolution Area," *J. Modern Optics* 55(4-5):671-681.

Escudero-Sanz et al. (Aug. 1999) "Off-Axis Aberrations of a Wide-Angle Schematic Eye Model," *J. Opt. Soc. Am. A* 16(8):1881-1891.

Eye Design Book, Table of Figures (Nov. 1, 2001) www.eyedesignbook.com/ch1/figuresch1.html.

Goncharov et al. (Aug. 2007) "Wide-Field Schematic Eye Models with Gradient-Index Lens," *J. Opt. Soc. Am. A* 24(8):2157-2174.

Goncharov et al. (Feb. 4, 2008) "Reconstruction of the Optical System of the Human Eye with Reverse Ray-Tracing," *Opt. Express* 16(3):1692-1703.

Goncharov et al. (2006) "Modal Tomography of Aberrations of the Human Eye," *Laser Phys.* 16(12):1689-1695.

Guirao et al. (Jun. 2000) "Corneal Wave Aberration from Videokeratography: Accuracy and Limitations of the Procedure," *J. Opt. Soc. Am. A* 17(6):955-965.

Hofer et al. (May 21, 2001) "Improvement in Retinal Image Quality with Dynamic Correction of the Eye's Aberrations," *Opt. Express* 8(11):631-643.

Huang (2004) "Computer Simulated Human Eye Modeling with GRIN Incorporated in the Crystalline Lens," Abstract 58 *J. Vis.* 4(11):58a.

Jones et al. (2005) "Refractive Index Distribution and Optical Properties of the Isolated Human Lens Measured Using Magnetic Resonance Imaging (MRI)," *Vision Res.* 45:2352-2366.

Kirkpatrick et al. (May 1983) "Optimization by Simulated Annealing," *Science* 220(4598):671-680.

Kirkpatrick (1984) "Optimization by Simulated Annealing: Quantitative Studies," *J. Stat. Phys.* 34(5-6):975-986.

Koretz et al. (Mar. 2004) "Scheimpflug and High-Resolution Magnetic Resonance Imaging of the Anterior Segment: A Comparative Study," *J. Opt. Soc. Am. A* 21(3):346-354.

Koretz (Jan. 2002) "Aging of the Human Lens: Changes in Les Shape Upon Accommodation and with Accommodative Loss," *J. Opt. Sci. Am A* 19(1):144-151.

Lambert et al. (May 12, 2008) "Applying SLODAR to Measure Aberrations in the Eye," *Opt. Exp.* 16(10):7309-7322.

Liang et al. (Nov. 1997) "Supernormal Vision and High-Resolution Retinal Imaging Through Adaptive Optics," *J. Opt. Soc. Am. A* 14(11):2884-2892.

Mallen et al. (2007) "Technical Note: Measurement of Retinal Contour and Supine Axial Length Using the Zeiss IOLMaster," *Ophthal. Physiol. Opt.* 27(4):404-411.

Metropolis et al. (1953) "Equation of State Calculations by Fast Computing Machines," *J. Chem. Phys.* 21(6):1087-1092.

Moffat et al. (2002) "Age-Related Changes in Refractive Index Distribution and Power of the Human Lens as Measured by Magnetic Resonance Micro-Imaging in vitro," *Vision Res.* 42:1683-1693.

Navarro et al. (Sep. 2007) "Adaptive Model of the Gradient Index of the Human Lens. II. Optics of the Accommodating Aging Lens," *J. Opt. Soc. Am. A* 24(9):2911-2920.

Navarro et al. (Aug. 2007) "Adaptive Model of the Gradient Index of the Human Lens. I. Optics Formulation and Model of Aging ex vivo Lenses," *J. Opt. Soc. Am. A* 24(8):2175-2185.

Navarro et al. (Feb. 2006) "Optics of the Average Normal Cornea from General and Canonical Representations of its Surface Topography," *J. Opt. Soc. Am. A* 23(2):219-232.

Navarro et al. (Sep. 1998) "Monochromatic Aberrations and Point-Spread Functions of the Human Eye Across the Visual Field," *J. Opt. Soc. Am. A* 15(9):2522-2529.

Navarro et al. (Aug. 1985) "Accommodation-Dependent Model of the Human Eye with Aspherics," *J. Opt. Soc. Am. A* 2(8):1273-1281.

Pomerantzeff (1971) "Wide Angle Optical Model of the Human Eye," *Ann. Ophthalmol.* 3(8):815-819.

Redding et al. (Apr. 1, 1993) "Hubble Space Telescope Prescription Retrieval," *Appl. Opt.* 32(10):1728-1736.

Roorda et al. (May 6, 2002) "Adaptive Optics Scanning Laser Ophthalmoscopy," *Opt. Express* 10(9):405-412.

Rosales et al. (2006) "Crystalline Lens Radii of Curvature from Purkinje and Scheimpflug Imaging," *J. Vis.* 6:1057-1067.

Rosales et al. (Mar. 2006) "Phakometry and Lens Tilt and Decentration Using a Custom-Developed Purkinje Imaging Apparatus: Validation and Measurements," *J. Opt. Soc. Am. A* 23(3):509-520.

Rouarch et al. (2008) "Propagation and Phase Reconstruction of Ocular Wavefronts with SAR Techniques," *J. Modern Optics* 55(4-5):717-725.

Rynders et al. (Oct. 1995) "Statistical Distribution of Foveal Transverse Chromatic Aberration, Pupil Centration, and Angle psi in a Population of Young Adult Eyes," *J. Opt. Soc. Am. A* 12(10):2348-2357.

Sakamoto et al. (Jan. 7, 2008) "Inverse Optical Design of the Human Eye Using Likelihood Methods and Wavefront Sensing," *Opt. Express* 16:304-314.

Sakamoto, (Jun. 2006) "Inverse Optical Design of the Human Eye Using Likelihood Methods and Wavefront Sensing" Poster Presented at Engineering the Eye II: Imaging the Retina, Conference, National University of Ireland, Galway, Ireland, Jun. 19-21.

Schwiegerling, J. (2004) "Purkinje Images," In; *Field Guide to Visual and Ophthalmic Optics* SPIE, pp. 39.

Schwiegerling et al. (Oct. 1995) "Representation of Videokeratoscopic Height Data with Zernike Polynomials," *J. Opt. Soc. Am. A* 12(10):2105-2113.

Sheehan et al. (Jun. 11, 2007) "Population Study of the Variation in Monochromatic Aberrations of the Normal Human Eye Over the Central Visual Field," *Opt. Express* 15(12):7367-7380.

Straub et al. (2001) "Design of a Compact Shack-Hartmann Aberrometer for Real-Time Measurement of Aberrations in Human Eyes" In; *Vision Science and Its Applications*, OSA Technical Digest (Optical Society of America, Washington DC) pp. 110-113.

Strenk et al. (May 1999) "Age-Related Changes in Human Ciliary Muscle and Lens: A Magnetic Resonance Imaging Study," *Invest. Ophthalmol. Visual Sci.* 40(6):1162-1169.

Tabernero et al. (Oct. 30, 2006) "Instrument for Measuring the Misalignments of Ocular Surfaces," *Opt. Express* 14(22):10945-10956.

Zhou et al. (May 2004) "Validation of a Combined Corneal Topographer and Aberrometer Based on Shack-Hartmann Wave-Front Sensing," *J. Opt. Soc. Am. A* 21(5):683-696.

\* cited by examiner

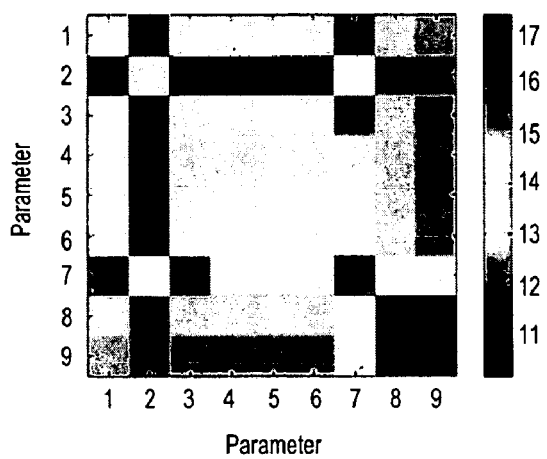 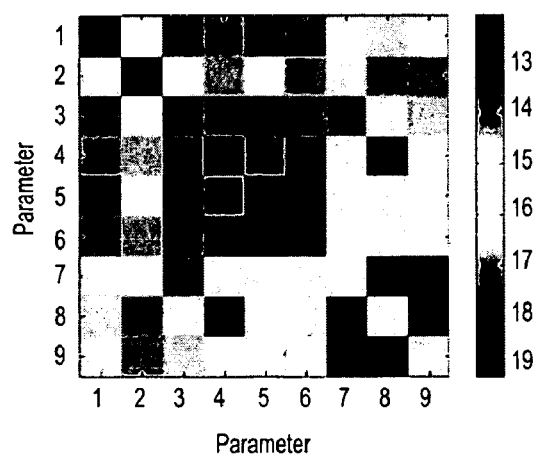
FIG. 5A        FIG. 5B

INVERSE OPTICAL DESIGN

CROSS-REFERENCE TO RELATED APPLICATIONS

This application takes priority from U.S. provisional application Ser. No. 60/934,786, filed Jun. 15, 2007, the disclosure of which is hereby incorporated by reference to the extent not inconsistent with the disclosure herein.

REFERENCE TO FEDERAL FUNDING SUPPORT

This invention was made with government support under Grant Numbers R37 EB000803 and T32 EB000809 awarded by NIH. The government has certain rights in the invention.

BACKGROUND OF THE INVENTION

The present invention generally relates to determination of patient-specific ocular parameters. The availability of a complete patient-specific eye model would provide many advantages in vision science and ophthalmology. A patient-specific eye model could be used as a basis for vision correction of higher-order aberrations in laser refractive surgery or with corrective lenses, since classical devices only measure and correct for basic refractive errors (i.e., defocus and astigmatism). Accurate determination of optical parameters in normal and abnormal eyes would be useful in developing data bases for clinical diagnosis of pathologies. Measurements of ocular surface misalignments would be useful after implantation of intraocular lenses in cataract surgery. Moreover, knowledge of the refractive index distribution in the lens would be beneficial in optical coherence tomography, which is based on interferometric reflectometry and index changes. It could also lead to a substantial improvement in retinal imaging.

In addition to improvements in vision correction and retinal imaging, the availability of patient-specific parameters could facilitate a broad range of ongoing vision science studies. Of interest is the in vivo gradient-index (GRIN) distribution and lenticular geometry of the human crystalline lens as a function of both age and accommodation, but this information has been difficult to obtain, and reliable measurements are scarce. While previous studies suggested that aspheric surfaces in the anterior segment and an effective refractive index for the lens are sufficient to model spherical aberration, lack of knowledge regarding the GRIN distribution precludes both the prediction of off-axis aberrations and study of dispersion in the lens, so experimental data are limited. A complete mapping of the human eye could also be used to evaluate intersubject variability and statistical variations, as well as vision performance and image quality in the central and peripheral visual fields, which could be enhanced by accurate measurement of the retinal curvature. Another fundamental study in physiological optics is how individual ocular components factor into the overall performance of the human eye and how such performance would change if one or more surfaces are altered, a critical element in surgical procedures.

Current theoretical eye models often lack contributions from asymmetry such as decentration of the lens or pupil, which manifest in the fovea as aberrations of non-axisymmetrical systems (e.g., coma, astigmatism, and transverse chromatic aberration) and may have a significant impact on ocular performance.

Several methods to determine aberrations of the eye are reported using wavefront data. These methods generally analyze wavefront data generated using a wavefront sensor, such as a Shack-Hartmann wavefront sensor, and model the wavefront using Zernike polynomials, for example, through known fitting techniques. The shape of the wavefront can be used to determine ocular aberrations. A technique has been described using wavefront data obtained at multiple excitation angles of the eye to generate information about the sources of aberration in the eye using mathematical modeling. (Goncharov, et al., Laser Physics, 2006, Vol. 16, No. 12, 1689-1695). U.S. Pat. No. 6,525,883 describes an apparatus used to measure one optical characteristic such as refracting power or shape of the cornea by illuminating a small area of the retina and calculation of Zernike factors from a split reflected light beam. U.S. Pat. No. 7,270,413 describes a method to calculate an optical characteristic of the eye by illuminating a portion of the retina, converting the reflected light into at least 17 beams and calculating Zernike coefficients using measured values of refractive power distribution and pupil diameters in the calculation. U.S. Pat. No. 6,802,609 describes methods of measuring a characteristic of the eye by illuminating a small region of the retina and calculating Zernike coefficients from the reflected data using a reference optical path in the system to account for equipment error. U.S. Pat. No. 6,273,566 describes a method for measuring a characteristic of the eye by calculating how an image is observed by the eye. U.S. Pat. No. 7,311,402 describes measuring the amount of scattering from the crystalline lens and retina in a wavefront sensing system. US 2007/0216866 describes using polarized light to calculate wavefront aberrations of an eye. US 2004/0257530 and US 2007/0222948 describe using Fourier transformation of wavefront data from the eye to calculate an optical surface model for use in laser eye surgery. U.S. Pat. No. 7,034,949 describes a method for determining the shape of a wavefront from an object by fitting Zernike polynomials to a diffraction pattern produced by the object. US 2004/0263779 describes a wavefront sensing system which uses a CMOS imaging system. U.S. Pat. No. 7,113,268 describes a wavefront sensing system which addresses spatio-temporal fluctuations (scintillation) in the intensity of the wavefront by using two intensity measurements. U.S. Pat. No. 5,384,455 describes methods for obtaining fine-resolution images in the presence of time-varying aberrations by collecting multiple images of the object and aberrations and estimating the object image. A mathematical wavefront aberration function was described using measured physical properties of anterior chamber length, axial length and cornea topography, and modeling light distribution in the eye (Rouarch, et al.,*Journal of Modern Optics*, 2008, Vol. 55, No. 4-5, 717-725). By illuminating the eye at different angles from the optical axis, measuring the wavefront aberrations of each beam and reverse ray tracing, a model eye was calculated (Goncharov, et al., *Optics Express*, 2008, Vol. 16, No. 3, 1692.

Techniques developed for use in astronomy have been adapted to ophthalmology. For example, modal tomography is used in astronomy to calculate a three-dimensional distribution of aberrations caused by turbulence using laser guide stars. A SLODAR (Slope Detection and Ranging) technique has been described which generates point source "stars" by using a reference laser beam to scatter from the retina and mathematical modeling the resultant waveforms (Lambert et al., *Optics Express*, 2008, Vol. 16, No. 10, 7309). A "prescription retrieval" system was used to estimate the optical parameters of optics on the Hubble Space Telescope as compared to the intended design parameters by varying parameters in an initial mathematical model of the optical component until images generated by the model match the actual images obtained from the actual optics system (Redding, et al., *Applied Optics*, 1993, Vol. 32, No. 10, 1728).

Current adaptive-optics ophthalmoscopes incorporating a Shack-Hartmann wavefront sensor (WFS) and wavefront corrector conjugated to a single surface of the eye offer high resolution, but over a very limited field-of-view (FOV) due to a form of anisoplanatism involving aberrations of the eye. Aberrations collected over different field positions on the retina result from the passage through different parts of the ocular media so that the adaptive-optics correction is valid only over a certain field area, referred to as the isoplanatic patch. One solution is to conjugate multiple wavefront sensors and correctors to various refractive surfaces in the eye, thereby increasing the isoplanatic patch size and enabling wide-field measurements, but choice of the optimal planes at which to conjugate the correctors would be facilitated by knowing the real eye structure of the individual. Mathematical averaging and physical methods (immersion of the eye) to enlarge the isoplanatic patch size have been proposed (Dubinin, et al., Journal of Modern Optics, 2008, Vol. 55, No. 4-5, 671-681).

BRIEF SUMMARY OF THE INVENTION

Provided is an apparatus and method for determining patient-specific ocular parameters using data obtained from light reflected and partly scattered from the retina. The description herein uses the phrase "reflected from the eye" and similar wording to indicate light that is technically reflected and scattered. More specifically, provided is an imaging apparatus for simultaneously determining optical parameters of the eye comprising: a light source for illuminating at least a portion of the eye pupil; an illumination optical system for directing light rays emitted from the light source into the eye; a light receiving optical system for guiding the light rays reflected from the eye to a detector unit, wherein the detector unit detects an image intensity distribution from the light rays reflected from the eye; and an arithmetic unit for determining optical characteristics of the eye by parameter estimation.

In one embodiment, the parameter estimation comprises a mathematical optimization algorithm. In one embodiment, the mathematical optimization algorithm is maximum-likelihood or maximum a posteriori estimation. In one embodiment, the mathematical optimization algorithm is non-linear least squares fitting. The light source may be any suitable source which illuminates at least a portion of the eye and does cause permanent damage to the eye structures. Light sources useful for such purposes are known in the art. Typically, a useful light source has a wavelength in the visible to infrared spectrum. In one embodiment, the illumination optical system illuminates the eye at an angle away from the optical axis of the eye. In one embodiment, the light receiving optical system is a lenslet array and detector assembly. In a particular embodiment, focal-plane data from a Shack-Hartmann wavefront sensor is used. In one embodiment, the light receiving optical system is more than one Shack-Hartmann wavefront sensors. The detector unit may be any suitable apparatus which detects sufficient information about the incident light to be useful in the methods described herein. In one embodiment, the detector unit is a CCD or CMOS array.

Also provided is a method for simultaneously determining ocular parameters of the eye comprising: illuminating at least a portion of the eye pupil with a light source; guiding light rays reflected from the eye to a detector unit; detecting an intensity distribution from the light rays reflected from the eye; determining optical parameters of the eye from the intensity distribution by parameter estimation. In one embodiment, the parameter estimation comprises an optimization method. In one embodiment, the optimization method is selected from the group consisting of: maximum likelihood estimation, nonlinear least squares fitting and maximum a posteriori estimation. In one embodiment, the determining step comprises: (a) generating a set of model ocular parameters using input from the eye reflection; (b) iteratively changing the model ocular parameters until the probability of the data conditional on the parameters is maximized.

The effect of various noise sources can be incorporated into the methods described herein, as known in the art. The data can be collected using a variety of methods and optical arrangements. The incident angle of light into the eye is an important parameter. Therefore, in one embodiment, the incident light is positioned off the optical axis of the eye. In one embodiment, data is obtained from more than one incident angle of light onto the eye. Another parameter which can be varied is the distance between the detector and the eye. If a lenslet array is used, the number and size of lenslets may be adjusted to provide the desired data from which to estimate the ocular parameters.

Optimization algorithms and their use are known in the art and require finding a maximum or minimum of some function, which can advantageously be done by simulated annealing, for example.

The number of ocular parameters which is determined by the techniques described here can vary, depending on the purposes of the determination. For example, only a few ocular parameters may be needed for a particular use, or a more complete set of ocular parameters may be required or desired. As known in the art, computational time increases with the number of variables used. In one embodiment, a sufficient number and type of ocular parameters to describe the eye are determined. In one embodiment, these parameters include cornea anterior radius, cornea posterior radius, lens anterior radius, lens posterior radius, cornea refractive index, lens refractive index, cornea thickness, lens thickness, effective refractive index, corneal posterior radius, anterior cornea conic constant, posterior cornea conic constant, anterior lens conic constant, posterior lens conic constant, and surface tilt, and any combination or subcombination of these or other ocular parameters. Other ocular parameters such as the asphericity of the external shape of the cornea and the crystalline lens with their local deformations are described by the coefficients of Zernike polynomials.

Although the description herein is primarily focused on optical design of the eye, it is understood that the methods and devices described here can be used to estimate geometrical parameters of any optical system, for example a GRIN distribution in a commercial lens.

BRIEF DESCRIPTION OF THE FIGURES

FIG. 5A shows the Fisher information matrix (FIM) for the system of beam angles on a logarithmic scale. FIG. 5B shows the inverse of the FIM, indicating coupling between parameter estimates and providing the Cramer-Rao bounds (CRBs) as the diagonal entries.

DETAILED DESCRIPTION OF THE INVENTION

Figure 1A:
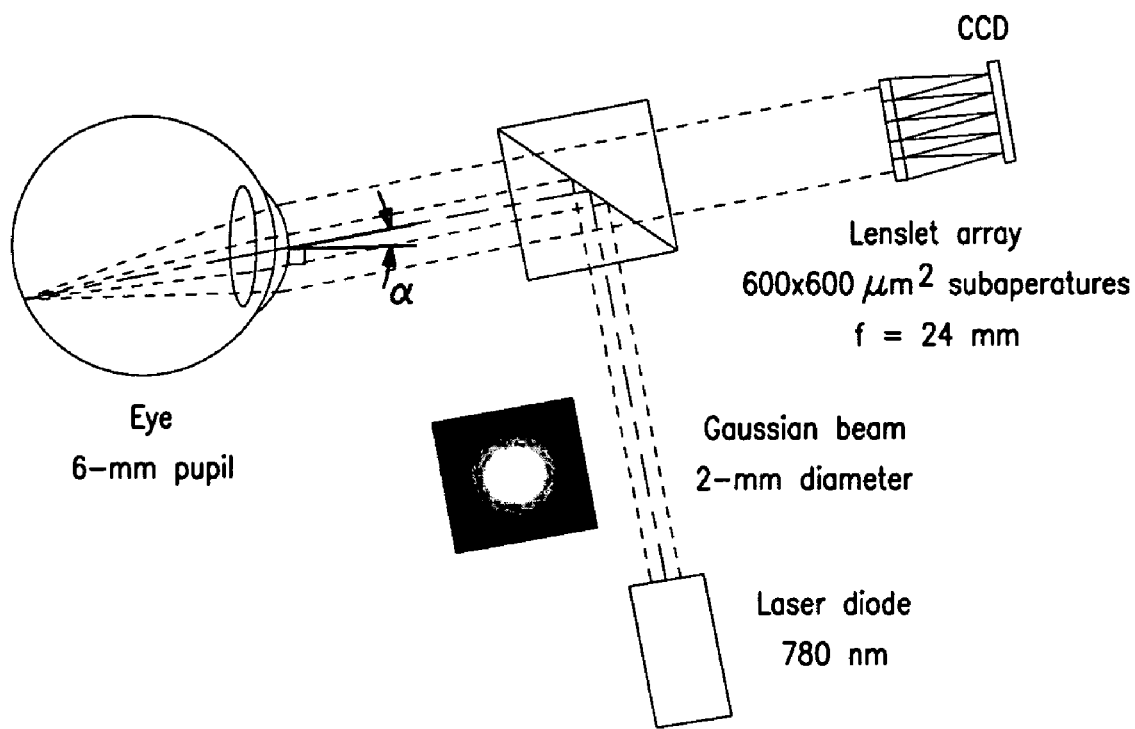
FIG. 1A shows a schematic of a Shack-Hartmann WFS system for the eye.

The following nonlimiting description is intended to provide examples of some embodiments of this invention and further information about the operation of the invention. Applicant does not intend to be bound by the theory presented.

The term "electromagnetic radiation" and "light" are used synonymously in the present description and refer to waves of electric and magnetic fields.

"Optical communication" refers to a configuration of two or more elements wherein one or more beams of electromagnetic radiation are capable of propagating from one element to the other element. Elements in optical communication may be in direct optical communication or indirect optical communication. "Direct optical communication" refers to a configuration of two or more elements wherein one or more beams of electromagnetic radiation propagate directly from a first device element to another without use of optical components for steering and/or combining the beams. "Indirect optical communication" on the other hand refers to a configuration of two or more elements wherein one or more beams of electromagnetic radiation propagate between two elements via one or more device components including, but not limited to, wave guides, fiber optic elements, reflectors, filters, prisms, lenses, gratings and any combination of these device components. Although the description is provided here with specific components, it is understood that other components such as fiber optics and waveguides may be used in the invention. The operation and use of other components is well understood by one of ordinary skill in the art. Also, the description is provided here with minimal optics components in the system. It is understood that other optics, such as filters, lens and other optics may be used with the system to provide the necessary or desired beam shaping and direction, for example. The operation and selection of such optics is well understood by one of ordinary skill in the art. In one embodiment, the methods and devices described herein are used in the visible portion of the spectrum. In one embodiment, the methods and devices described herein are used in the infrared portion of the spectrum.

A general description of the parameter estimation is described next, followed by more specific examples of the invention. The examples and description provided are not intended to limit the invention.

An accurate probability model for the eye is built by use of an optical design program. An optical model for the eye with unknown geometrical parameters (e.g., Navarro schematic eye model, although other eye models may be used) is used to start, since these parameters vary among patients. The data are chosen as the raw detector outputs from one or more Shack-Hartmann wavefront sensors, or other imaging systems that may be used. In contrast to conventional wavefront sensing, centroid estimation, wavefront reconstruction, and wavefront correction are not performed, since the process of centroid estimation results in severe information loss. Noise is added to the probability model, such as Poisson noise or Gaussian electronic noise, and a set of data is generated for a particular set of ocular parameters to describe an individual patient.

Once the data set is generated, estimating methods such as ML estimation are used to determine patient-specific parameters. In the case of uncorrelated Gaussian noise, ML estimation reduces to least-squares fitting between the data and the output of our optical design program. This final step is the inverse problem, involving an optimization algorithm that performs a search through parameter space (by proposing changes to the set of parameters) to find the set of parameters that maximizes the likelihood (the probability of occurrence of the data that are observed) or minimizes some other cost function. Simulated annealing is a feasible global optimization algorithm for dealing with large parameter spaces that have complicated surfaces, although other general algorithms are available as well, as known in the art. Each iteration in the inverse problem requires a solution to the forward problem, which in turn utilizes the optical design program to compute the output data for a particular set of parameters. The data are compared to the output of the program at each proposed point in parameter space, and the cost function of interest (e.g the likelihood) is determined. Finally, the optimization routine returns the values for the set of parameters that optimizes the cost function, and these values are presented as results.

Data-Acquisition

Figure 1B:
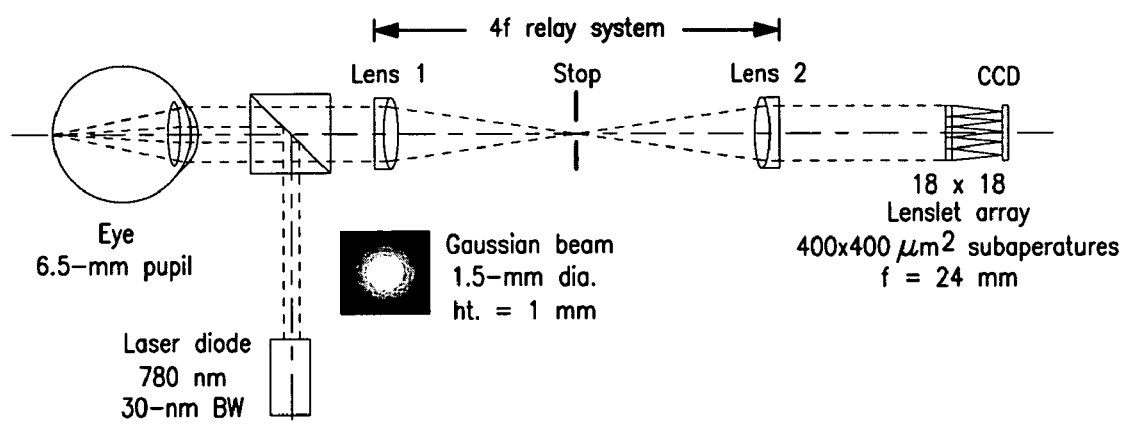
FIG. 1B shows a more specific schematic of a clinical Shack-Hartmann aberrometer.

The data consist of the raw detector outputs from a Shack-Hartmann WFS usually used for measurement of aberrations in human eyes, as illustrated in FIGS. 1A-B, rather than the wavefront estimate derived from the raw data. For the use described here, relay optics in the Shack-Hartmann WFS can be excluded. The center of the lenslet array is placed at a suitable distance from the corneal apex. In one embodiment, this distance is 10 mm from the corneal apex. This distance can vary. The number of lenslets can be varied. In one embodiment, an 18×18 lenslet array of 400 µm square lenslets was used. In another embodiment, an array of 600 µm square lenslets was used. In one embodiment, larger or smaller lenslets can be used. The light source, power, bandwidth, and wavelength can be varied, as known in the art. In one embodiment, a visible or infrared light is used. The power of the light source is sufficient to generate the desired data, but not so great as to cause damage to the eye. The angle between the laser beam and the optical axis of the eye is denoted $\alpha$. The angle between the laser beam and the optical axis of the eye can vary between +15 and −15 degrees, for example. The various effects of viewing the angle at an oblique angle, such as the elliptical appearance of the pupil of the eye due to perspective elongation, can be taken into account, as known in the art.

In the clinical system developed by Straub et al., a narrow collimated beam from a laser diode centered at 780 nm with a 30-nm bandwidth produces a point source on the retina, which acts as a laser beacon and fills the dilated pupil upon reflection. In our example, a single wavelength of 780 nm was used for simplicity and to reduce computation time. The eye was illuminated with a Gaussian beam (2 mm at FWHM) at multiple angles of 0, 6, and 12 degrees in the vertical direction to assess both on-axis and off-axis aberrations such as coma and astigmatism. The center of the beam was coincident with the intersection of the optic axis and anterior corneal surface. The aberrated retinal spot was treated as a perfect diffuse scatterer, but did not account for scattering within the ocular media or internal reflections. Furthermore, relay optics as used in the clinical configuration to conjugate the exit pupil of the eye to the WFS were excluded, and the lenslet array 10 mm away from the corneal apex. Relay optics can be used in this invention, as known in the art. Global wavefront tip and tilt were discarded by rotating the WFS for off-axis angles. A beamsplitter was not incorporated into this example, but a beamsplitter such as a pellicle beamsplitter to reduce unwanted back-reflections can be included. The lenslet array sampled the aberrated wavefront and produced a grid of focused spots on a detector placed in the focal plane. Generally, the amount of displacement of each spot from its ideal, on-axis location is proportional to the local average slope of the wavefront at the respective lenslet, while finer details of the aberrated wavefront manifest in the spot profiles. Therefore, both the spot positions and profiles provide useful information about aberrations in the eye. This method does not involve centroid estimation as in conventional wavefront sensing, and the data consist of all pixel intensity values in the focal plane of the WFS, which are referred to as the raw detector outputs. For this example, a commercially available micro-WFS, consisting of an array of 600×600 μm² lenslets with a focal length of 24 mm was used. The detector pixels had a pitch of 10 μm, and the peak SNR was $10^3$.

An optical design program was designed in MATLAB, which performs non-paraxial ray-tracing through quadric surfaces, and simulated a trial set of data for ocular parameters comparable to those in the Navarro wide-angle schematic eye model, as provided in Table 1. Other eye models may be used, as known in the art. The chromatic dispersion model developed by Atchison and Smith was used to calculate refractive indices at 780 nm. Therefore, an effective refractive index for the crystalline lens is used in this example. A GRIN distribution can also be incorporated, if desired. In addition, the lens was decentered by 0.20 mm in the horizontal direction and −0.10 mm in the vertical direction, which agrees with the experimental range of crystalline lens misalignments. WFS data was generated by tracing a 256×256 grid of rays, although about 60% of the rays survived the double-pass after the random retinal reflection and vignetting at the pupil.

TABLE 1

Geometry of Eye Model Used in Simulation at 780 nm

| Surface | Radius [mm] | Thickness [mm] | Conic Constant | Refractive Index | Optical Medium |
|---|---|---|---|---|---|
| Anterior cornea | 7.46 | 0.554 | −0.24 | 1.3729 | Cornea |
| Posterior cornea | 6.72 | 3.17 | 0 | 1.3329 | Aqueous |
| Pupil | Infinity | 0 | 0 | 1.3329 | Aqueous |
| Anterior lens | 10.35 | 3.97 | −3.1304 | 1.4138 | Lens |
| Posterior lens | −6.28 | 16.61 | −0.97 | 1.3311 | Vitreous |
| Retina | −12.00 | N/A | 0 | N/A | N/A |

Next, it was assumed that the system is not photon-starved and Gaussian statistics were used to represent electronic noise. For detector elements that are i.i.d. (independent and identically distributed) and noise that is independent of the illumination level, the probability density function (PDF) from which the data are drawn is given by $$pr(g \mid 0) = \prod_{m=1}^{M} \frac{1}{\sqrt{2\pi\sigma^2}} \exp\left[-\frac{[g_m - \bar{g}_m(0)]^2}{2\sigma^2}\right], \quad (1)$$

where g is the M×1 vector set of random data, θ is the set of estimable parameters, and $\sigma^2$ is the variance in each detector element. Furthermore, overbars are used to denote means, such that $\bar{g}_m^{(\Theta)}$ represents the average value of the $m^{th}$ detector element evaluated at θ. Since the noise is zero-mean Gaussian, $\bar{g}_m^{(\Theta)}$ is simply the output of the optical design program. The variance was calculated to obtain a peak SNR of $10^3$ and noise was applied in the data using a Gaussian random number generator.

Maximum-Likelihood Estimation

After generating the data, knowledge of the values of selected parameters was disregarded and the selected parameters were estimated by maximizing the likelihood. Essentially, ML estimation returns the θ argument which maximizes the probability of occurrence of the observed data, defined as $$\hat{\theta}_{ML} \equiv \underset{\theta}{\mathrm{argmax}}\, pr(g \mid \theta), \quad (2)$$

where $\hat{\theta}$ represents an estimate of the vector set of parameters. Since the logarithm increases monotonically with its argument, Eq. (2) can be rewritten as $$\hat{\theta}_{ML} \equiv \underset{\theta}{\mathrm{argmax}}\, \ln[pr(g \mid \theta)]. \quad (3)$$

For a purely Gaussian noise model with i.i.d. detector elements, it can be shown that ML estimation according to Eq. (3) reduces to nonlinear least-squares fitting between the data and the output of the optical design program:

$$\hat{\theta}_{ML} = \underset{0}{\mathrm{argmin}} \sum_{m=1}^{M} [g_m - \bar{g}_m(0)]^2. \quad (4)$$

Immediate advantages are that ML estimation is efficient (i.e., unbiased and yields the best possible variance) if an efficient estimator exists, and that it is asymptotically unbiased as more photons are acquired. However, one challenge is that an accurate probability model must be used that includes all sources of randomness (e.g., photon noise and electronic noise) as well as fluctuations of ocular aberrations associated with live imaging of the eye, including the tear film effect.

Fisher Information

The performance of the ML estimator can be analyzed with the Fisher information matrix (FIM), denoted F, because it describes the ability to estimate a vector set of parameters and is related to the sensitivity of the data to changes in those parameters. For a vector parameter of P real components, the FIM is a P×P symmetric matrix with components given by $$F_{jk} = \left\langle \left[\frac{\partial}{\partial \theta_j} \ln pr(g \mid 0)\right] \left[\frac{\partial}{\partial \theta_k} \ln pr(g \mid 0)\right] \right\rangle_{g \mid 0}, \quad (5)$$

where the angle brackets denote the average. Mathematically, it is the covariance matrix of the gradient of the logarithm of the likelihood. Therefore, off-diagonal entries in the FIM indicate coupling between different pairs of parameters;

stronger coupling leads to greater noise in the parameter estimates. For Gaussian i.i.d. data, the FIM components reduce to $$F_{jk} = \frac{1}{\sigma^2} \sum_{m=1}^{M} \frac{\partial \bar{g}_m(0)}{\partial \theta_j} \frac{\partial \bar{g}_m(0)}{\partial \theta_k}, \quad (6)$$

which depend on the average data vector evaluated at the set of parameters and are inversely proportional to the variance in the detector elements [33].

Inversion of the FIM provides the Cramer-Rao lower bound (CRB) on the variance (i.e. the theoretical minimum possible variance) of the parameter estimates. It is well known that the variance of any unbiased estimate obeys the Cramér-Rao inequality:

$$[K_\theta]_{nn} = \text{Var}\{\hat{\theta}_n\} \geq [F^{-1}]_{nn}. \quad (7)$$

For an efficient estimator, the inverse of the FIM is the covariance matrix of the parameter estimates; thus, its off-diagonal elements represent coupling between these estimates. The FIM, its inverse, and the CRBs were calculated for the chosen subset of parameters using the optical design program.

In general, the FIM can be computed for any system configuration and therefore used to design and optimize the system that acquires the WFS data to be used as input to the inverse optical design, prior to clinical application. That system is referred to as the inverse design system. Adjustable system parameters to increase Fisher information include the beam size, beam angle, lenslet array geometry, detector element spacing, and variance in the detector elements. Additionally, data from multiple beam angles can serve to decouple pairs of ocular parameters in the FIM, which could improve parameter estimability. The embodiment of using multiple beam angles is included here, and can be carried out without undue experimentation by one of ordinary skill in the art.

Results and Discussion

Forward Model and Trial Data

Figure 2:
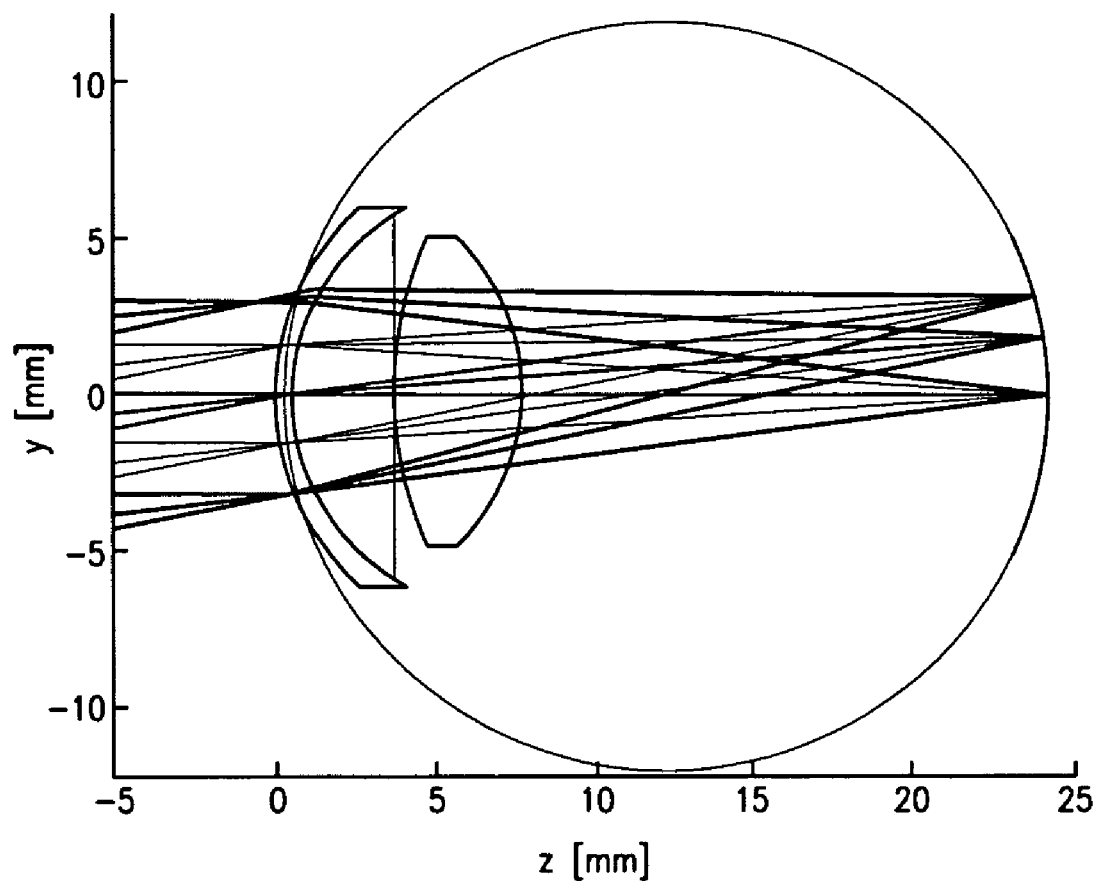
FIG. 2 shows the geometrical eye model used to generate WFS data, corresponding to ocular parameters in Table 1. Sample rays for 0, 6, and 12 degrees are shown. The y-axis corresponds to the vertical direction.
Figure 3A:
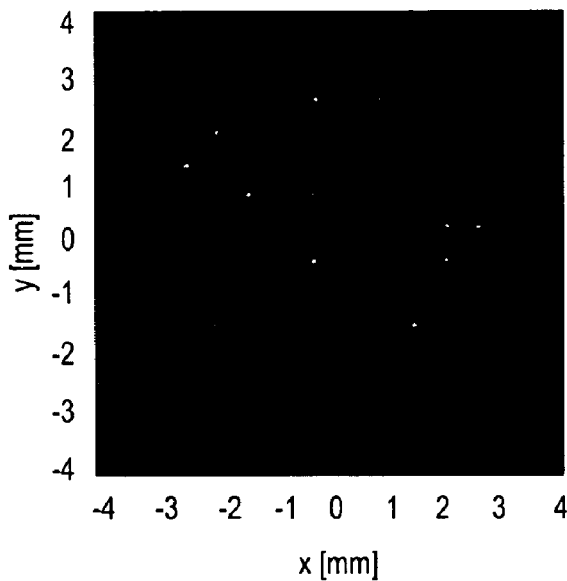
FIGS. 3(A-C) shows corresponding WFS data used as input to inverse optical design, for beam angle: (a) 0 degrees, (b) 6 degrees, and (c) 12 degrees.
Figure 3B:
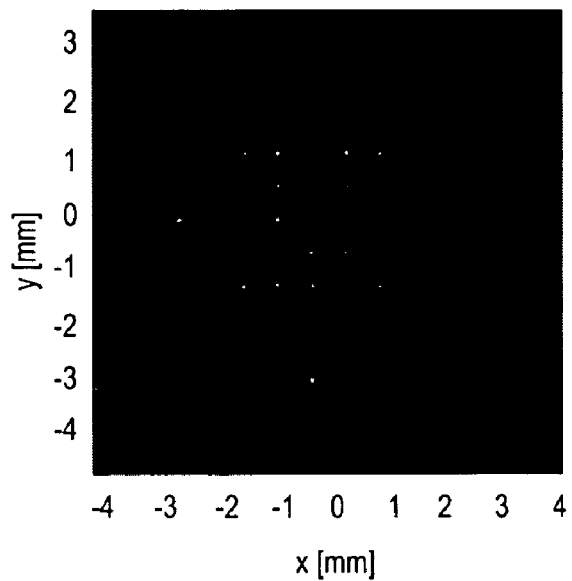
Figure 3C:
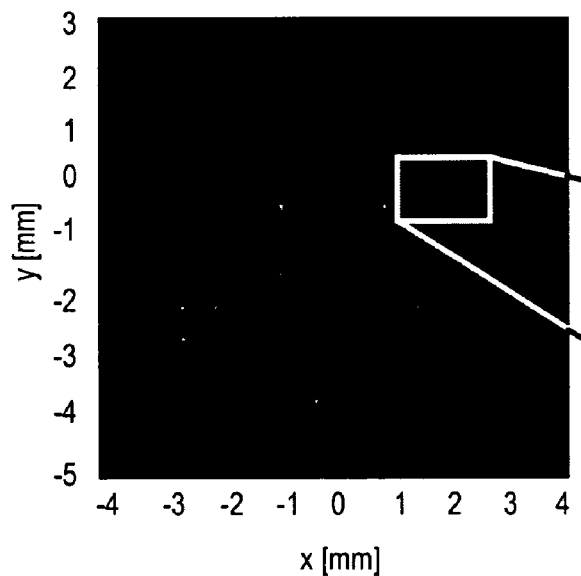
Figures 4A, 4B, 4C:
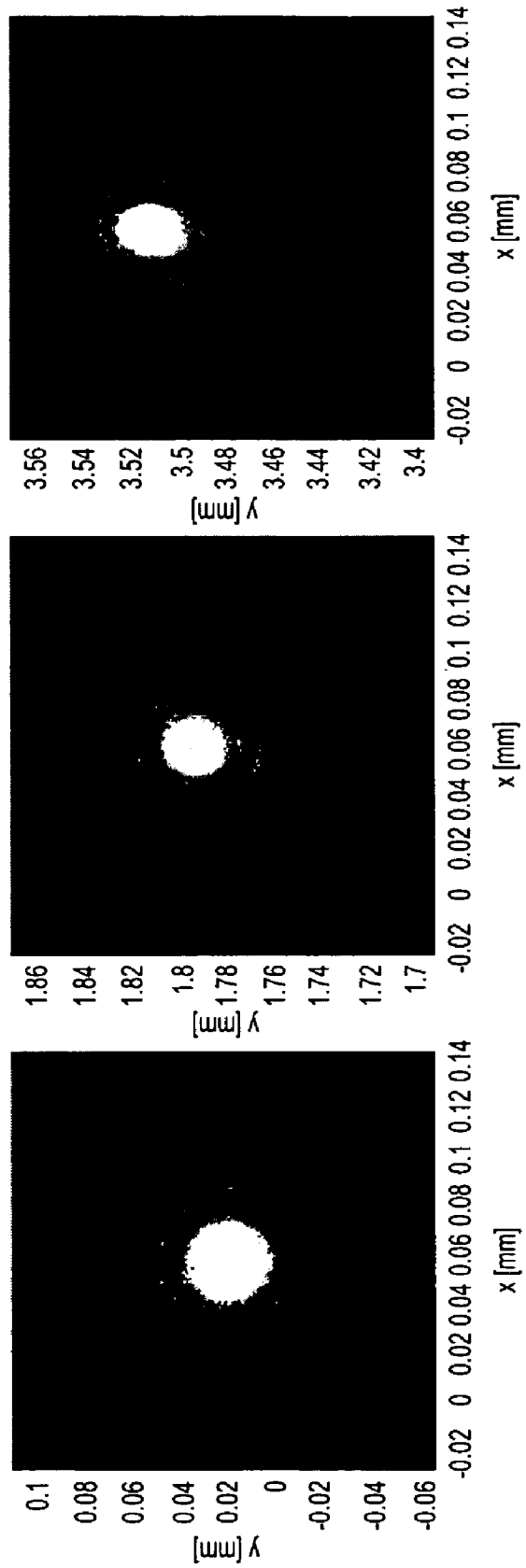
FIGS. 4(A-C) shows focal spots on the retina due to the source beam for angle: (a) 0 degrees, (b) 6 degrees, and (c) 12 degrees.

The geometrical eye model corresponding to the ocular parameters provided in Table 1 and crystalline lens decentrations stated earlier is illustrated in FIG. 2, which was generated using the optical design program. This program performs non-paraxial ray-tracing through second-order surfaces (e.g., conic or biconic surfaces) using the vector form of Snell's law. Sample rays for the multiple beam angles (i.e. 0, 6, and 12 degrees) used in this study are also plotted. The trial set of WFS data used as input to the inverse optical design problem are provided in FIGS. 3(A-C). The respective focal spots on the retina are shown in FIGS. 4(A-C) with the coordinate system centered on the optical axis, such that the position on the retina can be read from the axes.

Fisher Information and Cramer-Rao Bounds

In this study, the optical model used a reduced set of ocular parameters including the posterior radius, thickness, and refractive index of the cornea, the thickness and index of the anterior chamber, and the anterior and posterior radius, thickness, and equivalent index of the crystalline lens. The FIM of the system including data from all beam angles is displayed on a logarithmic scale shown in FIG. 5A, with values ranging from 10.145 to 17.375. This matrix is order-specific, and the indices of the estimated parameters are listed in Table 1. Note that the $jk^{th}$ entry has units of [units of $j^{th}$ parameter]$^{-1}$ [units of $k^{th}$ parameter]$^{-1}$. The large values in the FIM indicate that the data are very sensitive to changes in the parameters, but that the magnitudes of off-diagonal entries reveal a high degree of undesired coupling between pairs of parameters. This is intuitive since first-order geometrical parameters combine to form various optical quantities, such as refractive index and thickness in optical path length, and curvatures and indices in optical power. An adverse effect of parameter coupling is that an error in one parameter estimate will cause errors in the estimates of all other parameters, while it introduces many local minima in the likelihood surface.

The FIM was inverted as shown in FIG. 5A, also on a logarithmic scale, and the diagonal entries were read off to determine the CRB for each parameter estimate. The corresponding standard deviations (i.e., square-roots) are given in Table 2. These diminutive values permit the estimation of parameters to high precisions even under pessimistic noise levels since a peak SNR of only $10^3$ was implemented, and the theoretical lower bound on the variances can immediately be improved by decreasing the variance in the detector pixels. However, the performance of the ML estimator relies greatly on an accurate forward model of the system, particularly when real data are used. Complexity can be added to the basic likelihood model by incorporating other noise sources, coherence properties of the source as well as the retinal reflection, a GRIN distribution in the crystalline lens, the Stiles-Crawford effect, scattering within the ocular media, Fresnel reflections between the ocular surfaces, topography of the corneal surface, and the optical effect of the tear film. These effects are known in the art. Stray light, misalignments, or other effects that may contribute to estimation errors can be taken into account by methods known in the art.

Parameter Estimation

Algorithms that implement a likelihood approach to estimating parameters perform a search through parameter space to find a point that maximizes the probability of generating the observed data. Virtually all search algorithms locate an extremum via iterative methods that execute in a variable number of steps, depending on the starting location, the complexity of the probability surface, and values selected for convergence factors. One challenge in this method of parameter estimation is that the estimation step is very time consuming, especially since a complicated surface with many local features and strong coupling between parameters is used. A proficient global search algorithm tailored to the probability surface can be used and will provide advantages in the computation resources needed. The algorithm used may involve prior information obtained from statistical studies or by other reliable modalities such as corneal topography, which can be used to select a starting point or put limits on the parameter values to narrow the search space. An approximate method based on optimization with reverse ray-tracing can be used to provide a starting point for the likelihood approach. This study used a custom simplex algorithm for the optimization and a nearby starting point to avoid stagnation in local basins of the surface.

Figure 6:
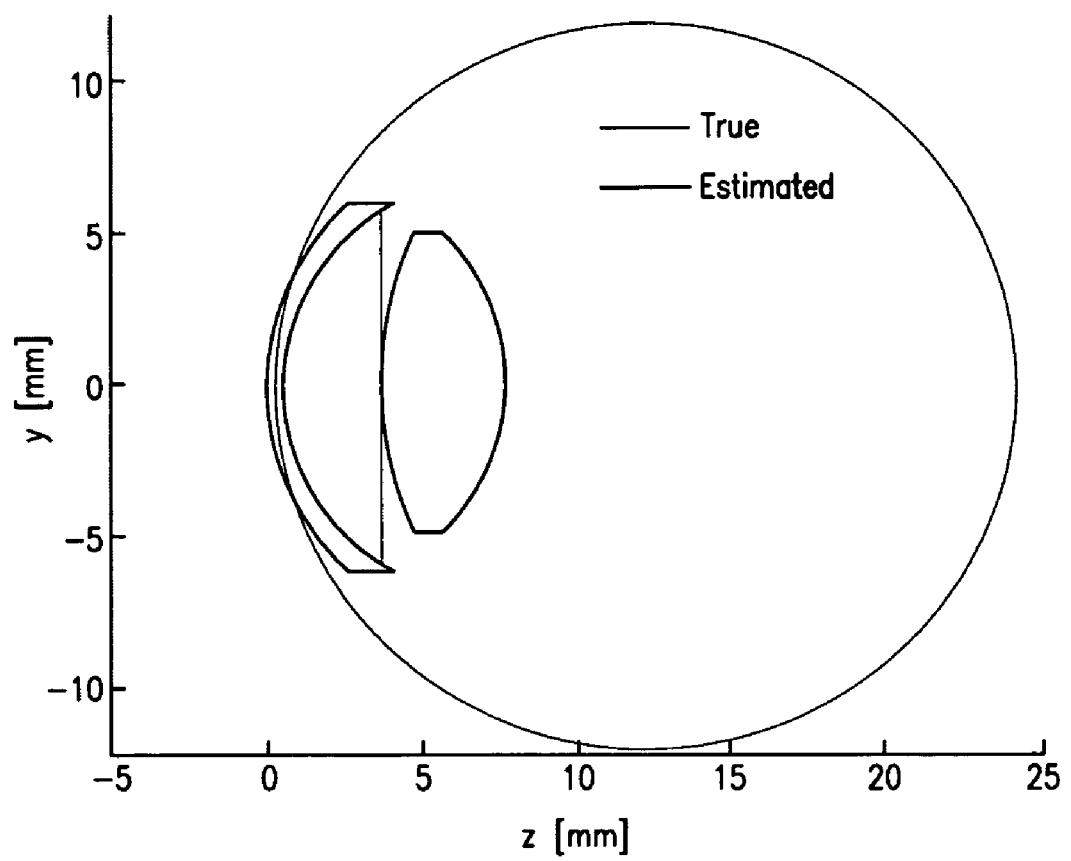
FIG. 6 shows a reconstructed eye model of the estimated parameters, superimposed with the true values in the data.

The estimated parameters from the analysis described here are listed in Table 2, including the true values used to generate data, the starting point in the ML search, the final estimates, and the fractional error in each estimate. The parameters were estimated to two or three decimal places of accuracy for radii and thicknesses and four to five decimal places for refractive indices. All errors were within a fraction of a percent, indicating very good agreement between the true and estimated values. The reconstructed eye model shows precise overlap, as illustrated in FIG. 6. Although the corneal anterior radius was not estimated assuming that its value is known from direct measurements, it was plotted in the reconstruction to indicate the estimated corneal thickness.

TABLE 2

Estimated ocular parameters, including the values used to generate the data, standard deviations computed from the lower CRBs, starting point in the ML search, parameter estimates, and fractional error in the estimates.

| No. | Parameter | Value | CRB$^{1/2}$ | Starting point | ML Estimate | Fractional error |
|---|---|---|---|---|---|---|
| 1 | Corneal posterior radius [mm] | 6.72 | $8.2 \times 10^{-7}$ | 6.65 | 6.720616 | $9.2 \times 10^{-5}$ |
| 2 | Lens anterior radius [mm] | 10.35 | $5.0 \times 10^{-7}$ | 10.30 | 10.352853 | $2.8 \times 10^{-4}$ |
| 3 | Lens posterior radius [mm] | −6.28 | $8.3 \times 10^{-7}$ | −6.30 | −6.280767 | $1.2 \times 10^{-4}$ |
| 4 | Cornea thickness [mm] | 0.554 | $9.3 \times 10^{-7}$ | 0.55 | 0.554192 | $3.5 \times 10^{-4}$ |
| 5 | Anterior chamber thickness [mm] | 3.17 | $8.6 \times 10^{-7}$ | 3.12 | 3.170405 | $1.3 \times 10^{-4}$ |
| 6 | Lens thickness [mm] | 3.97 | $1.1 \times 10^{-6}$ | 4.00 | 3.972967 | $8.9 \times 10^{-5}$ |
| 7 | Cornea refractive index | 1.3729 | $8.4 \times 10^{-9}$ | 1.3771 | 1.372967 | $4.9 \times 10^{-5}$ |
| 8 | Anterior chamber refractive index | 1.3329 | $7.4 \times 10^{-9}$ | 1.3374 | 1.332901 | $7.5 \times 10^{-7}$ |
| 9 | Lens refractive index | 1.4138 | $8.9 \times 10^{-9}$ | 1.4100 | 1.413806 | $4.2 \times 10^{-6}$ |

When normalized by the detector variance and total number of elements, the sum-of-squares described in Eqn. 4 is 401.779 at the starting point, 1.65236 at the termination point in the optimization, and 0.998794 at the true global minimum. (As the number of pixels increases, the true minimum should approach unity using the normalization stated above.) Other ML search algorithms can be used in finding the true minimum and achieving the Cramér-Rao bounds.

As mentioned previously, this is a very complicated and high-dimensional probability surface with many local minima and strong coupling between various ocular parameters. In the example shown herein, a basic simplex search algorithm was used to estimate a reduced set of ocular parameters from simulated wavefront sensor data using maximum-likelihood (ML) estimation. Simplex algorithms essentially perform straightforward minimization, in which the search only accepts downhill moves along the surface to be minimized. This process leads to the quickest nearby solution, even if it corresponds to a local, but not optimal, solution. To circumvent this problem, a nearby starting point was used in the parameter-space to avoid stagnation in local basins of the surface, simply to demonstrate the ability of ML estimation in solving the inverse problem at hand. However, in clinical practice, the values of the parameters are truly unknown and such a good starting point can not be assumed. One solution is to use a global optimization algorithm that can deal with a complicated surface containing many local optima.

One technique that can be used for global optimization is simulated annealing. This technique was originally developed by Metropolis et al. (1953) in the context of statistical mechanics, an application of probability theory which includes a mathematical framework for dealing with large populations of atoms or molecules. A simple algorithm was created to simulate the thermodynamic equation of state for a complex system of atoms by Monte Carlo sampling. However, the general applicability to optimization problems was later recognized by Kirkpatrick et al. (1983, 1984) by using the Metropolis algorithm and making clever analogies to statistical mechanics while simulating the physical process of annealing as in materials science. A detailed discussion of this technique is provided in the references included herein.

Simulated annealing is a stochastic algorithm that provides a good approximation to the global optimum of a given function in a high-dimensional search space with many local extrema, since transitions out of a local optimum are always possible during the search based on a probability criterion. It is able to process objective functions with high degrees of nonlinearities, discontinuities, and randomness due to noise sources. It can also distinguish between large-scale features and finer "wrinkles" in the function, both of which became evident in the problem here. Furthermore, the parameter-space of interest can contain arbitrary boundary conditions and constraints, allowing prior information about the human eye to be incorporated, including known statistical variations across a population. Most important, simulated annealing guarantees the true solution under very stringent conditions, but satisfying these requirements would lead to the global optimum much too slowly for practical use. Instead, the conditions are relaxed to trade-off computational time and optimality of the solution. Even with this compromise if simulated annealing does not find the true solution, it will find a near-optimal one. Although simulated annealing is very promising in many aspects, its major criticism is high computational demand compared to straightforward optimization methods.

An adaptive form of simulated annealing developed by Corana et al. (1987), which considers unique physical constraints (e.g., finite ranges) for each parameter, as well as different sensitivities of the cost function along different parameter axes was used. This particular algorithm also optimizes computational time by attempting to maintain a one-to-one ratio between the number of accepted and rejected moves, thereby searching the parameter-space efficiently. The same set of ocular parameters was estimated as before, although the true values were slightly modified. Furthermore, the same system configuration as described above was used, except a single beam angle of 0 degrees was used and traced a 128×128 grid of rays to decrease computational time. Since there is a twelve-fold reduction in information compared to the initial study, the Cramér-Rao lower bound (CRB) was noticeably larger, as shown in the table below. In the search space, the value of the normalized objective function was 226.74 at the upper limit, 313.09 at the lower limit, and 35.709 at the starting point. At the termination point of the optimization, the function value was 1.0012, yielding a fractional error of $2.2 \times 10^{-3}$ compared to that of the true minimum, 0.99898. Therefore, using simulated annealing allows a significantly larger search space to be explored that is comparable to known statistical variations and use of a reasonable starting point, yet still obtain accurate estimates of ocular parameters by means of inverse optical design.

| No. | Parameter | Value | CRB$^{1/2}$ | Lower limit | Starting point | Upper limit | ML Estimate | Fractional error |
|---|---|---|---|---|---|---|---|---|
| 1 | Corneal posterior radius [mm] | 6.38 | $1.6 \times 10^{-6}$ | 5.75 | 6.25 | 6.75 | 6.416812 | $5.8 \times 10^{-3}$ |
| 2 | Lens anterior radius [mm] | 10.85 | $1.0 \times 10^{-6}$ | 10.50 | 11.00 | 11.50 | 10.819210 | $2.8 \times 10^{-3}$ |
| 3 | Lens posterior radius [mm] | −5.92 | $3.3 \times 10^{-6}$ | −6.50 | −6.00 | −5.50 | −5.906822 | $2.2 \times 10^{-3}$ |
| 4 | Cornea thickness [mm] | 0.554 | $1.7 \times 10^{-6}$ | 0.54 | 0.55 | 0.56 | 0.557371 | $6.1 \times 10^{-3}$ |
| 5 | Anterior chamber thickness [mm] | 3.37 | $2.7 \times 10^{-6}$ | 3.00 | 3.50 | 4.00 | 3.373267 | $9.7 \times 10^{-4}$ |
| 6 | Lens thickness [mm] | 4.09 | $2.3 \times 10^{-6}$ | 3.50 | 4.00 | 4.50 | 4.081044 | $2.2 \times 10^{-3}$ |
| 7 | Cornea refractive index | 1.3729 | $1.3 \times 10^{-7}$ | 1.3700 | 1.3750 | 1.3800 | 1.374107 | $8.8 \times 10^{-4}$ |
| 8 | Anterior chamber refractive index | 1.3329 | $1.2 \times 10^{-8}$ | 1.3300 | 1.3350 | 1.3400 | 1.332878 | $1.7 \times 10^{-5}$ |
| 9 | Lens refractive index | 1.4138 | $2.5 \times 10^{-8}$ | 1.4100 | 1.4150 | 1.4200 | 1.413540 | $1.8 \times 10^{-4}$ |

REFERENCES

1. J. Tabernero, A. Benito, V. Nourrit, and P. Artal, "Instrument for measuring the misalignments of ocular surfaces," Opt. Express 14, 10945 (2006). http://www.opticsexpress.org/abstract.cfm?id=116620
2. P. Rosales and S. Marcos, "Phakometry and lens tilt and decentration using a custom-developed Purkinje imaging apparatus: validation and measurements," J. Opt. Soc. Am. A 23, 509 (2006).
3. P. Rosales, M. Dubbelman, S. Marcos, and G. L. Van der Heijde, "Crystalline lens radii of curvature from Purkinje and Scheimpflug imaging," J. Vis. 6, 1057 (2006).
4. C. E. Jones, D. A. Atchison, R. Meder, and J. M. Pope, "Refractive index distribution and optical properties of the isolated human lens measured using magnetic resonance imaging (MRI)," Vision Res. 45, 2352 (2005).
5. B. A. Moffat, D. A. Atchison, and J. M. Pope, "Age-related changes in refractive index distribution and power of the human lens as measured by magnetic resonance microimaging in vitro," Vision Res. 42, 1683 (2002).
6. H. Hofer, L. Chen, G. Yoon, B. Singer, Y Yamauchi, and D. R. Williams, "Improvement in retinal image quality with dynamic correction of the eye's aberrations," Opt. Express 8, 631 (2001). http://www.opticsexpress.org/abstract.cfm?id=64333
7. A. Roorda, F. Romero-Borja, W. Donnelly, III, H. Queener, T. Hebert, and M. Campbell, "Adaptive optics scanning laser opthalmoscopy," Opt. Express 10, 405 (2002). http://www.opticsexpress.org/abstract.cfm?id=68843
8. J. Liang, D. R. Williams, and D. Miller, "Supernormal vision and high-resolution retinal imaging through adaptive optics," J. Opt. Soc. Am. A 14, 2884 (1997).
9. R. Navarro, J. Santamaría, and J. Bescós, "Accommodation-dependent model of the human eye with aspherics," J. Opt. Soc. Am. A 2, 1273 (1985).
10. M. Dubbelman and G. L. Van der Heijde, "The shape of the aging human lens: curvature, equivalent refractive index and the lens paradox," Vision Res. 41, 1867 (2001).
11. R. Navarro, E. Moreno, and C. Dorronsoro, "Monochromatic aberrations and point-spread functions of the human eye across the visual field," J. Opt. Soc. Am. A 15, 2522 (1998).
12. M. T. Sheehan, A. V. Goncharov, V. M. O'Dwyer, V. Toal, and C. Dainty, "Population study of the variation in monochromatic aberrations of the normal human eye over the central visual field," Opt. Express 15, 7367 (2007).
13. I. Escudero-Sanz and R. Navarro, "Off-axis aberrations of a wide-angle schematic eye model," J. Opt. Soc. Am. A 16, 1881 (1999).
14. E. Mallen and P. Kashyap, "Technical note: measurement of retinal contour and supine axial length using the Zeiss IOLMaster," Ophthal. Physiol. Opt. 27, 404 (2007).
15. P. Artal and A. Guirao, "Contributions of the cornea and the lens to the aberrations of the human eye," Opt. Lett. 23, 1713 (1998).
16. S. Bará and R. Navarro, "Wide-field compensation of monochromatic eye aberrations: expected performance and design trade-offs," J. Opt. Soc. Am. A 20, 1 (2003).
17. M. Rynders, B. Lidkea, W. Chisholm, and L. N. Thibos, "Statistical distribution of foveal transverse chromatic aberration, pupil centration, and angle psi in a population of young adult eyes," J. Opt. Soc. Am. A 12, 2348 (1995).
18. D. Redding, P. Dumont, and J. Yu, "Hubble Space Telescope prescription retrieval," Appl. Opt. 32, 1728 (1993).
19. G. R. Brady and J. Fienup, "Phase retrieval as an optical metrology tool," in Optifab: Technical digest, SPIE Technical Digest TD03, pp. 139-141 (2005).
20. J. Schwiegerling, Field Guide to Visual and Ophthalmic Optics (SPIE, 2004).
21. J. F. Koretz, S. A. Strenk, Lawrence M. Strenk, and John L. Semmlow, "Scheimpflug and high-resolution magnetic resonance imaging of the anterior segment: a comparative study," J. Opt. Soc. Am. A 21, 346 (2004).
22. M. Dubbelman, H. A. Weeber, G. L. Van der Heijde, and H. J. Völker-Dieben, "Radius and asphericity of the posterior corneal surface determined by corrected Scheimpflug photography," Acta. Opthalmol. Scand. 80, 379 (2002).
23. S. A. Strenk, J. L. Semmlow, L. M. Strenk, P. Munoz, J. Gronlund-Jacob, and J. K. DeMarco, "Age-related changes in human ciliary muscle and lens: a magnetic resonance imaging study," Invest. Opthalmol. Visual Sci. 40, 1162 (1999).
24. J. Schwiegerling, J. E. Greivenkamp, and J. M. Miller, "Representation of videokeratoscopic height data with Zernike polynomials," J. Opt. Soc. Am. A 12, 2105 (1995).
25. R. Navarro, L. Gonzalez, and J. L. Hernandez, "Optics of the average normal cornea from general and canonical representations of its surface topography," J. Opt. Soc. Am. A23, 219 (2006).
26. F. Zhou, X. Hong, D. T. Miller, L. N. Thibos, and A. Bradley, "Validation of a combined corneal topographer and aberrometer based on Shack-Hartmann wave-front sensing," J. Opt. Soc. Am. A 21, 683 (2004).
27. A. Guirao and P. Artal, "Corneal wave aberration from videokeratography: accuracy and limitations of the procedure," J. Opt. Soc. Am. A 17, 955 (2000).
28. J. Straub, J. Schwiegerling, and A. Gupta, "Design of a compact Shack-Hartmann aberrometer for real-time measurement of aberrations in human eyes" in Vision Science and Its Applications, OSA Technical Digest (Optical Society of America, Washington D.C., 2001), pp. 110-113.

29. D. A. Atchison and G. Smith, "Chromatic dispersions of the ocular media of human eyes," J. Opt. Soc. Am. A 22, 29 (2005).
30. A. V. Goncharov and C. Dainty, "Wide-field schematic eye models with gradient-index lens," J. Opt. Soc. Am. A 24, 2157 (2007).
31. R. Navarro, F. Palos, and L. M. González, "Adaptive model of the gradient index of the human lens. I. optics formulation and model of aging ex vivo lenses," J. Opt. Soc. Am. A 24, 2175 (2007).
32. R. Navarro, F. Palos, and L. M. González, "Adaptive model of the gradient index of the human lens. II. optics of the accommodating aging lens," J. Opt. Soc. Am. A 24, 2911 (2007).
33. H. H. Barrett, C. Dainty, and D. Lara, "Maximum-likelihood methods in wavefront sensing: stochastic models and likelihood functions," J. Opt. Soc. Am. A 24, 391 (2007).
34. A. V. Goncharov, M. Nowakowski, M. T. Sheehan, and C. Dainty, "Reconstruction of the optical system of the human eye with reverse ray-tracing," Opt. Express (to be published).
35. J. A. Sakamoto, H. H. Barrett, and A. V. Goncharov, "Inverse optical design of the human eye using likelihood methods and wavefront sensing," Opt. Express 16, 304-314 (2008).
36. N. Metropolis, A. W. Rosenbluth, M. N. Rosenbluth, and A. H. Teller, "Equation of state calculations by fast computing machines," J. Chem. Phys. 21, No. 6, 1087-1092 (1953).
37. S. Kirkpatrick, C. D. Gelatt, Jr., M. P. Vecchi, "Optimization by simulated annealing," Science 220, No. 4598, 671-680 (1983).
38. H. H. Barrett and K. J. Myers (2004), Foundations of Image Science, Wiley, N.J.
39. A. Corana, M. Marchesi, C. Martini, and S. Ridella, "Minimizing multimodal functions of continuous variable with the 'simulated annealing' algorithm," ACM Transactions on Mathematical Software 13, No. 3, 262-280 (1987).

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a structure is claimed, it should be understood that structures known in the prior art, including certain structures disclosed in the references disclosed herein (particularly in referenced patent documents), are not intended to be included in the claim.

When a group of substituents is disclosed herein, it is understood that all individual members of those groups and all subgroups of the group members, and classes of group members that can be formed using the substituents are disclosed separately. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of optics and other materials are intended to be exemplary, as it is known that one of ordinary skill in the art can name the same optics and materials differently. One of ordinary skill in the art will appreciate that methods, device elements, starting materials, imaging methods, and analysis methods other than those specifically exemplified can be employed in the practice of the invention without resort to undue experimentation. All art-known functional equivalents, of any such methods, device elements, starting materials, imaging methods, and analysis methods are intended to be included in this invention. Whenever a range is given in the specification, for example, a distance range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a structure or in a description of elements of a device, is understood to encompass those structures and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The definitions are provided to clarify their specific use in the context of the invention.

We claim:

1. An imaging apparatus for simultaneously determining the parameters in an optical model of the eye using inverse optical design comprising:
   a light source for illuminating at least a portion of the eye pupil;
   an illumination optical system for directing light emitted from the light source into the eye;
   a light receiving optical system for guiding the light reflected from the eye to a detector unit, wherein the detector unit detects an image intensity distribution produced by the light reflected from the eye;
   an optical model of the eye having unknown geometrical and optical parameters;

an arithmetic unit for determining all parameters in the optical model of the eye using inverse optical design by parameter estimation using the pixel outputs from the detector unit, as opposed to aberration or wavefront information derived from those outputs, and a mathematical optimization algorithm.

2. The apparatus of claim 1, wherein the light source is a laser having wavelength in the visible to infrared spectrum.

3. The apparatus of claim 1, wherein the illumination optical system illuminates the eye at an angle away from the optical axis of the eye.

4. The apparatus of claim 1, wherein the light receiving optical system is a lenslet array and detector assembly.

5. The apparatus of claim 4, wherein the light receiving optical system is a lenslet array.

6. The apparatus of claim 4, wherein the light receiving optical system is more than one lenslet array.

7. The apparatus of claim 1, wherein the detector unit is a CCD or CMOS array.

8. The apparatus of claim 1, wherein parameters of the eye are one or more selected from the group consisting of: corneal anterior radius, corneal posterior radius, lens anterior radius, lens posterior radius, corneal thickness, anterior chamber thickness, lens thickness, corneal refractive index, anterior chamber refractive index, lens refractive index, effective refractive index, anterior cornea conic constant, posterior cornea conic constant, anterior lens conic constant, posterior lens conic constant, gradient-index (GRIN) distribution in the crystalline lens, surface decentration, and surface tilt.

9. The imaging apparatus of claim 1, wherein the mathematical optimization algorithm performs a search through parameter space by proposing changes to a set of parameters to find the set of parameters that minimize a statistically based cost function.

10. The imaging apparatus of claim 9, wherein the cost function is selected from: the negative of the likelihood (probability of the data given the model parameters), the negative logarithm of the likelihood, the negative of the posterior probability (likelihood times the prior probability of the model parameters), the negative logarithm of the posterior probability, the sum of the squares of the differences between observed raw data values and the means of these values as predicted by the model parameters, or the sum of the squares of the differences between observed raw data values and the means of these values as predicted by the model parameters, weighted by a function of the statistical variance of the data values.

11. The imaging apparatus of claim 9, wherein the mathematical optimization algorithm uses prior information obtained from statistical studies or by other modalities such as corneal topography to obtain a starting point or put limits on the parameter values to narrow the search space.

12. An imaging apparatus for simultaneously determining the complete set of geometrical or optical parameters of a model eye using inverse optical design comprising:
a light source for illuminating at least a portion of the eye pupil;
an illumination optical system for directing light-emitted from the light source into the eye;
a light receiving optical system for guiding light reflected from the eye to a detector unit, wherein the detector unit detects an image intensity distribution produced by the light reflected from the eye;
a model eye having a set of unknown geometric and optical parameters;
an arithmetic unit for determining all parameters of the model eye using inverse optical design by parameter estimation using the pixel outputs from the detector unit, as opposed to aberration or wavefront information derived from those outputs, and a mathematical optimization algorithm, wherein the optimization algorithm implements maximum-likelihood or maximum a posteriori estimation.

13. The apparatus of claim 12, wherein the mathematical optimization algorithm is nonlinear least-squares fitting.

14. A method for simultaneously determining geometrical and/or optical parameters of the eye using inverse optical design from a model eye comprising:
generating input data by:
illuminating at least a portion of the eye pupil with a light source;
guiding light reflected from the eye to a detector unit;
detecting an intensity distribution produced by light reflected from the eye;
determining geometrical or optical parameters of the eye from the intensity distribution using inverse optical design by parameter estimation, whereby the parameter estimation comprises:
(a) providing an optical model for the eye with unknown model ocular parameters;
(b) generating a trial set of model ocular parameters using pixel outputs from the detector unit, as opposed to aberration or wavefront information derived from those outputs;
(c) iteratively changing the model ocular parameters until the probability of the data conditional on the model ocular parameters is maximized.

15. The method of claim 14, wherein the parameter estimation comprises an optimization method.

16. The method of claim 15, wherein the optimization method is selected from the group consisting of: maximum-likelihood estimation, nonlinear least-squares fitting and maximum a posteriori estimation.

17. An imaging apparatus for simultaneously determining geometrical or optical parameters of the eye using inverse optical design comprising:
a light source having an emission wavelength in the visible to infrared spectrum for illuminating at least a portion of the eye pupil;
an illumination optical system for directing light emitted from the light source into the eye;
a lenslet array to detect an image intensity distribution produced by the light reflected from the eye;
a mathematical optimization algorithm for determining geometrical or optical parameters of the eye using inverse optical design from the intensity distribution, wherein the mathematical optimization algorithm comprises:
(a) providing an optical model for the eye with unknown model ocular parameters;
(b) using an optical design program to determine the data in one or more output planes for an arbitrary system configuration;
(c) defining a quantitative objective function using maximum-likelihood estimation, maximum a posteriori estimation, or nonlinear least-squares fitting; and
(d) solving the inverse problem using an optimization algorithm that proposes changes to the system configuration, whereby at least one geometrical or optical parameter is determined.

18. An imaging apparatus for simultaneously determining the parameters in an optical model of a lens system using inverse optical design comprising:

a light source for illuminating at least a portion of the pupil of the lens system;

an illumination optical system for directing light emitted from the light source into the lens system;

a light receiving optical system for guiding the light exiting the lens system to a detector unit, wherein the detector unit detects an image intensity distribution produced by the light reflected from the lens system;

an optical model of the lens system having unknown geometrical and optical parameters;

an arithmetic unit for determining all parameters in the optical model of the lens system using inverse optical design by parameter estimation using the pixel outputs from the detector unit, as opposed to aberration or wavefront information derived from those outputs, and a mathematical optimization algorithm.

19. The apparatus of claim 18, wherein the light source is a laser having wavelength in the visible to infrared spectrum.

20. The apparatus of claim 18, wherein the illumination optical system illuminates the lens system at an angle away from the optical axis of the lens system.

21. The apparatus of claim 18, wherein the light receiving optical system is a lenslet array and detector assembly.

22. The apparatus of claim 21, wherein the light receiving optical system is a lenslet array.

23. The apparatus of claim 21, wherein the light receiving optical system is more than one lenslet array.

24. The apparatus of claim 18, wherein the detector unit is a CCD or CMOS array.

25. The apparatus of claim 18, wherein parameters of the lens system are one or more of the following types: radius of curvature, thickness, conic constant, refractive index, effective refractive index, gradient-index (GRIN) distribution, surface decentration, and surface tilt.

26. The imaging apparatus of claim 18, wherein the mathematical optimization algorithm performs a search through parameter space by proposing changes to a set of parameters to find the set of parameters that minimize a statistically based cost function.

27. The imaging apparatus of claim 26, wherein the cost function is selected from: the negative of the likelihood (probability of the data given the model parameters), the negative logarithm of the likelihood, the negative of the posterior probability (likelihood times the prior probability of the model parameters), the negative logarithm of the posterior probability, the sum of the squares of the differences between observed raw data values and the means of these values as predicted by the model parameters, or the sum of the squares of the differences between observed raw data values and the means of these values as predicted by the model parameters, weighted by a function of the statistical variance of the data values.

28. The imaging apparatus of claim 26, wherein the mathematical optimization algorithm uses prior information obtained from manufacturer specifications or by other methods of optical testing to obtain a starting point or put limits on the parameter values to narrow the search space.

\* \* \* \* \*